United States Patent [19]

Gould et al.

[11] Patent Number: 5,215,904
[45] Date of Patent: Jun. 1, 1993

[54] METHOD FOR PRODUCING A RECOMBINANT MAMMAL IN VIVO

[75] Inventors: Michael N. Gould; Bingcheng Wang, both of Madison, Wis.

[73] Assignee: Wisconsin Alumni Research Foundation, Madison, Wis.

[21] Appl. No.: 303,863

[22] Filed: Jan. 27, 1989

[51] Int. Cl.$^5$ ............................................... C12N 15/00
[52] U.S. Cl. ..................... 435/172.3; 800/2; 800/DIG. 2; 435/948; 935/57
[58] Field of Search ............ 800/2, DIG. 1, DIG. 2; 435/172.3, 948, 69.1; 935/11, 32, 57

[56] References Cited

U.S. PATENT DOCUMENTS 4,650,764  3/1987  Temin et al. .
4,736,866  4/1988  Leder et al. .
4,873,316  10/1989  Meade et al. ....................... 530/412

OTHER PUBLICATIONS

Edwards et al., Oncogene 2: 407–412 (1988).
Zwiebel et al., Proc. Am. Assoc. Cancer Res. Annu. Meeting vol. 31(0): 212 (1990).
Simons et al., Nature 328: 530–532 (1987).
D. Turner et al., 328 Nature 131–136 (1987).
J. Price et al., 84 P.N.A.S. USA 156–160 (1987).
J. Wilson et al., 85 P.N.A.S. USA 4421–4425 (1988).
J. Wilson et al., 85 P.N.A.S. USA 3014–3018 (1988).
J. Dougherty et al., 84 P.N.A.S. USA 1197–1201 (1987).
A. Miller et al., 12 Som. Cell Mole. Gen. 175–183 (1986).
M. Eglitis et al., 6 BioTech. 608–614 (1988).
M. Bender et al., 61 J. Virol. 1639–1646 (1987).
D. Markowitz et al., 62 J. Virol. 1120–1124 (1988).
R. Cone et al., 8 Mol. Cell. Biol. 1036–1044 (1988).
M. Ben-David, 83 Endocrinology 1217–1223 (1968).
K. Gordon et al., 5 Bio/Technology 1183–1187 (1987).
A. Dannenberg et al., Methods For Studying Mononuclear Phagocytes, pp. 375–396 (N.Y. Acad. Press) (1981).

Primary Examiner—Jasemine C. Chambers
Attorney, Agent, or Firm—Quarles & Brady

[57] ABSTRACT

A method for producing a recombinant mammal in vivo is disclosed. The mammal has a mammary gland, with mammary epithelial cells lining a duct in that gland One increases the rate of mitosis of the mammary epithelial cells (e.g. by using perphenazine or a mitogen), and one then exposes the mammary epithelial cells in vivo in the gland to a recombinant vector (e.g. a retrovirus vector). The mammary epithelial cells can be pretreated (or simultaneously treated) with polybrene to facilitate infection by virus vectors, and the vector can have a signal sequence which causes foreign proteinaceous material to be secreted into the milk produced by the mammary gland. Also disclosed are recombinant non-human mammals produced by such methods and novel milk products that they produce.

5 Claims, 2 Drawing Sheets

METHOD FOR PRODUCING A RECOMBINANT MAMMAL IN VIVO This invention was made with U.S. government support awarded by the National Institute of Health (NIH), grant numbers CA44387 and CA28954. The U.S. government has certain rights in this invention.

This invention relates to recombinant DNA technology. More particularly it relates to a method for rendering mammary glands of living animals recombinant so that they are able to produce foreign proteins.

BACKGROUND OF THE INVENTION

It is now possible to introduce foreign genes of interest into animal chromosomes in vitro (e.g. in the test tube) using various known vectors (see e.g. U.S. Pat. Nos. 4,650,764 and 4,736,866; J. Wilson et al., 85 P.N.A.S. U.S.A. 3014–3018 and 4421–4425 (1988); J. Dougherty et al., 84 P.N.A.S. U.S.A. 1197–1201 (1987)). In some in vitro approaches, genes are placed in somatic cells (e.g. cells from the liver), while in other approaches, genes are placed in fertilized germ cells to create transgenic animals. The disclosures of these articles and patents, and of all other articles recited herein, are incorporated by reference as fully set forth herein. However, such in vitro prior art techniques can be time consuming and require great laboratory skill to use, can (in the case of transgenic techniques) result in all of the germ and somatic cells throughout the body expressing the foreign gene (with resulting potential side effects and safety concerns), and can lead to difficulties in obtaining government approvals (since progeny will also carry the modified gene in their chromosome).

While there therefore have been efforts to transform selected animal cells in vivo (using *live* animals), difficulties have arisen in achieving this result. One stumbling block related to the need for a high titer of virus vector (e.g. retrovirus vector) where virus vectors were used. Accordingly, there were efforts to increase the titers of vectors. See e,g. J. Price et al., 84 P.N.A.S. U.S.A. 154–160 (1987).

While high titer retrovirus vectors have recently been used (albeit inefficiently) in vivo to infect certain neonatal retinal cells adjacent the brain (see D. Turner et al., 328 Nature 131–136 (1987)), other cells of live animals, and cells of live animals that are past the neonatal stage, have proved resistant to in vivo recombinant techniques.

Thus, it can be seen that a need exists for the development of efficient means for rendering other cells (particularly mammary epithelial cells) recombinant in vivo.

SUMMARY OF THE INVENTION

One embodiment of the present invention provides a method for producing a recombinant mammal in vivo. The mammal is of the type having a mammary gland with mammary epithelial cells lining a duct in that gland. One first increases the rate of mitosis (cell division) of the mammary epithelial cells, and then exposes in vivo at least one of the mammary epithelial cells in the gland to a recombinant vector which has a gene coding for a proteinaceous material of interest. The vector renders the epithelial cell able to express the foreign proteinaceous material of interest.

The vector is preferably a retrovirus vector and the exposing step can comprise inserting the vector into the duct by injecting the vector directly into the duct along the axis of the duct outlet. Various means of increasing the rate of mitosis are disclosed, such as injecting the mammal under the skin with perphenazine (a drug which inhibits suppressors that naturally suppress the rate of natural prolactin production), not aborting a pregnancy of the mammal, or exposing the epithelial cell to an agent for stimulating mammary mitosis that is selected from the group of prolactin, estrogen, growth hormone, placental lactogenic hormones, and progesterone. The epithelial cells are preferably also exposed to polybrene prior to (or during) exposure to the vector.

It will be appreciated that the proteinaceous material is expressed directly into the cell itself. This can provide a foreign proteinaceous material that the cell can use. For example, the cell can be made to produce an enzyme or a lactogenic hormone.

In the alternative, the vector can have a recombinant gene sequence in which there is a foreign gene coding for proteinaceous material of interest preceded by genetic information coding for a specific signal sequence which facilitates (directly or indirectly) secretion. After the epithelial cell has been rendered recombinant by the vector, the cell will be able to secret the proteinaceous material of interest into the duct. Since milk is also secreted into the duct, the milk will then automatically have the "additive". By milking the animal (e.g. a cow or goat), the animal can become a factory for foreign gene production. One can then purify out the proteinaceous material (e.g. interferon). It should be noted that eukaryotic production systems are preferred for producing certain proteins that cannot successfully be made in bacterial systems.

Alternatively, the additives can be left in the milk. One can then consume the milk (either in the form of milk or in the form of milk products such as cheese).

Another potential use would be to have the vector code for anti-sense genetic sequences, thereby modifying the content of the milk being produced The milk would then not have an additive. Rather, the ratio of major milk proteins would be altered. Thus, custom cheeses and custom milks could be produced from high volume producing cow lines that were previously limited to only certain types of milk and cheese.

Genes could also be included in the vector which code for proteinaceous materials useful in other parts of the body (e.g. hormones that stimulate milk or meat formation). Appropriate modification of the vector by placing an appropriate signal sequence immediately upstream of the coding gene could then permit the protein to more readily enter the bloodstream. This could eliminate the need for routine hormone injections for certain domestic animals (e.g. cows, goats, pigs).

Yet another use would be to assist with research that tests the effect of certain genes (or proteins coded for thereby).

In another aspect of the invention, the invention provides a non-human mammal having recombinant mammary epithelial cells that were rendered recombinant in vivo by the above techniques. Yet another aspect of the invention provides milk produced by the recombinant non-human mammal described above.

It will be appreciated that various problems were faced and overcome by the inventors in attempting to render recombinant in vivo mammary epithelial cells. For example, there was the problem of how to uniformly expose mammary epithelial cells to a high concentration of vector. Another problem was how to render the cells receptive to infection (e.g. vector integration) by the vector. Another problem was how to localize the modifications to cells located in the mammary gland. Another problem was how to cause the additional protein to be secreted into the milk. There were various other problems that were solved as well.

The objects of the invention therefore include:

(a) providing a method of the above kind which permits the rendering of mammary epithelial cells recombinant;

(b) providing a method of the above kind which is inexpensive to use and efficient;

(c) providing a method of the above kind in which the resulting animal is recombinant with respect to mammary epithelial cells but not with respect to germ cells;

(d) providing recombinant non-human mammals produced by methods of the above kind in which the mammals are capable of secreting the foreign gene of interest into their milk;

(e) providing milk produced by recombinant non-human mammals of the above kind.

These and still other objects and advantages of the present invention will be apparent from the description which follows.

DESCRIPTION OF THE PREFERRED EMBODIMENTS

A. The Vector

Figure 1:
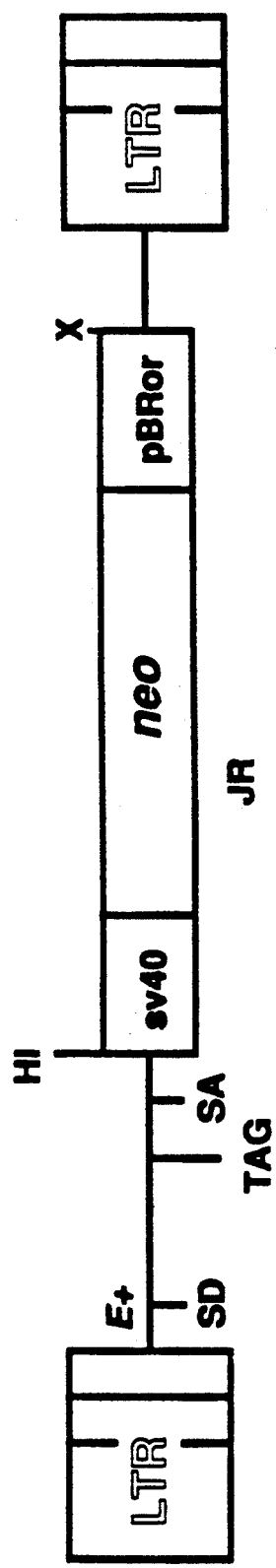
FIG. 1 depicts the gene sequence of vector JR.

A preferred vector was constructed by replacing sequences from BclI to XhoI of LNL6 (M.A. Bender et al., 61 J. Virol. 1639-1646 (1987)) with BamHI to XhoI fragment from the BAG vector (J. Price et al., 84 P.N.A.S. U.S.A. 154-160 (1987)). The newly derived vector, ("JR", see FIG. 1) has the following properties:

(1) high titer due to the presence of additional gag sequences which are required for efficient packaging;

(2) lack of $Pr60^{gag}$ expression because of the AUG to TAG amber mutation;

(3) an independent neomyocin selection marker;

(4) a convenient cloning site (BamHI) for the gene of interest; and (5) it is replication incompetent.

If desired, internal promoters can be inserted into the vectors upstream of the coding gene and between the LTR's to minimize the effects of LTR suppression.

Figure 2:
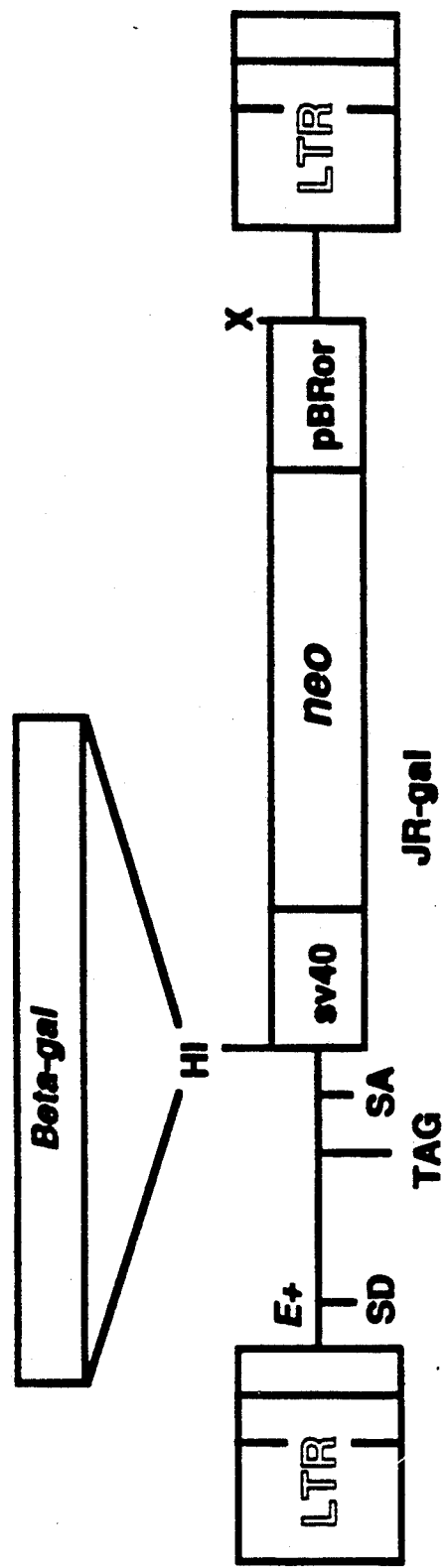
FIG. 2 depicts the gene sequence of vector JR-gal.

As a test system, the *E. coli* β-galactosidase gene was used as the one coding for the foreign gene of interest. The PstI to SalI fragment of pBAG containing gag-Beta-gal fusion coding protein sequences were cloned into the BamHI site of JR to yield JR-gal (see FIG. 2). The β-gal gene, a reporter gene, was used because its product can easily be detected in cells by histochemical staining using methods that are well known. However, it will be appreciated that various other foreign genes of interest can be inserted in this particular vector (or in various other vectors).

B. Establishment Of Producer Cell Lines

JR-gal was then used to transfect packaging cell line PA317 using conventional techniques. PA317 is a known modified mouse embryo packaging cell line derived from NIH 3T3 TK−. It supplies trans proteins for retrovirus vector production. PA317 is an amphotropic packaging cell line (permitting the retrovirus to infect a wide variety of different types of cells). A deposit of JR-gal in PA317 has been made with the American Type Culture collection, Rockville, Md., as ATCC #CRL 9995. It was deposited on Jan. 20, 1989. Samples from the deposit will be made available in accordance with U.S. patent law requirements and the requirements of any foreign patent laws. No patent license is intended by such availability. It will be appreciated that the specific packaging line or vector is not critical to the invention, and various other packaging cell lines and vectors that are the most suited to particular hosts can be used in any given situation. See generally A. Miller et al., 12 Som. Cell. Mol. Gene. 175-183 (1986).

C. Increasinq The Rate Of Mitosis 50-60 day old female adult rats were treated with three daily doses of perphenazine (day 1, 1 mg/kg of body weight, days 2 and 3, 5 mg/kg of body weight). Perphenazine was injected under the skin on the back of the animal. For other species, appropriate doses can be determined by running a simple series of tests using varied concentrations

D. Obtaininq The Vector Stock

The procedures for obtaining vector stock from the frozen deposited JR-gal in PA317 line is as follows: One gradually warms the deposit to 37° C. After washing with tissue culture media, one grows the line in tissue culture media and collects the virus stock.

To concentrate the virus stock one hundred fold, one takes 30 ml of the virus stock layered over 4 ml of 20% sucrose in PBS and then spins it in a Beckman SW 28 rotar for 2.5 hours. The pellets generated thereby can be gently resuspended in a medium or PBS in 1/100th of the original volume.

E. Injection

To assist in in vivo infection, polybrene can be added to the concentrated virus stock to 80 μg/ml. For rats, the day after the last injection of perphenazine, one injects 20 μl of the concentrated virus stock/polybrene mixture directly into the central duct of each mammary gland. For rats, the tip of the mammary nipple had to be opened up to permit easy injection. For cows (or other large mammals), one can directly inject the drug into the natural duct opening. For different animals, a simple series of control tests will establish concentrations and doses. Multiple injections may well be preferable in larger animals.

The above research led to recombinant mammary epithelial cells (confirmed by surgery on the rat and histochemical confirmatory staining of the cells looking for the presence of the β galactosidase enzyme). The techniques for such staining are described in A. Donnelly et al., Methods For Studying Mononuclear Thagocytes pp. 375-396 (N.Y. Acad. Press) (1981).

F. Secretion Into The Milk

If desired, one can insert a tissue plasminogen activator signal peptide sequence (see K. Gordon et al., 5 Biol. Technology 1183-1187 (1987)) immediately upstream of the gene of interest on the recombinant vector. This signal is known to cause mammary epithelial cells to secrete material into the duct (and thus the milk). It will also be appreciated that various other signal sequences may be developed which will permit the material to be directed to the animal's bloodstream (and thus other parts of the body).

It will therefore be appreciated that the present invention provides a means of modifying in vivo a selected set of the cells of a mammal, while leaving the rest of the animal's cells non-recombinant. The fact that the particular cells are mammary cells has significant additional utility because the protein can be secreted into the milk. Further, the fact that the mammary epithelial cells line the central duct makes it possible for there to be very efficient and simple delivery. Those who have little skill in laboratory techniques will still be able to use the invention to modify cow and other animals. Further, safety and regulatory concerns are considerably reduced when compared to many transgenic in vitro techniques since germ cell chromosomes remain unaffected.

It will be appreciated that the above describes only the preferred embodiments of the invention. A number of other modifications and changes are within the scope of the invention and are intended to be included within the scope of the claims. Thus, the claims should be looked to in judging the scope of the invention.

We claim:

1. A method for producing a recombinant mammal in vivo, the mammal being of the type having an adult mammary gland with mammary epithelial cells lining a duct in that gland, the method comprising the steps of:
    increasing the rate of mitosis of the mammary epithelial cells by administering an effective amount of an agent for stimulating mitosis; and
    then exposing in vivo mammary epithelial cells in the gland to a recombinant retroviral vector which has a gene coding for a protein of interest by inserting the vector into the duct;
    whereby the vector renders the epithelial cells able to express the protein of interest.

2. The method of claim 1, wherein the rate of mitosis is increased by exposing the mammary epithelial cells to perphenazine.

3. The method of claim 1, wherein the rate of mitosis is increased by expsoing the epithelial cells to an agent for stimulating mitosis that is selected from the group of prolactin, estrogen, growth hormone, placental lactogenic hormone, and progesterone.

4. The method of claim 1, wherein the exposing step comprises exposing the mammary epithelial cells to polybrene.

5. The method of claim 1, wherein said vector further comprises a signal sequence which enables said epithelial cells to secrete said protein of interest into the duct.

* * * * *

UNITED STATES PATENT AND TRADEMARK OFFICE
CERTIFICATE OF CORRECTION

PATENT NO. : 5,215,904

DATED : June 1, 1993

INVENTOR(S) : Michael N. Gould, et al.

It is certified that error appears in the above-identified patent and that said Letters Patent is hereby corrected as shown below:

Column 6, line 16            "expsoing" s/b "exposing"

Signed and Sealed this

Eleventh Day of January, 1994

*Attest:*

BRUCE LEHMAN

*Attesting Officer*      *Commissioner of Patents and Trademarks*